United States Patent [19]

Schwartz

[11] 4,311,512

[45] * Jan. 19, 1982

[54] BACTERICIDAL WATER-SOLUBLE COMPLEXES

[76] Inventor: Herbert Schwartz, 1963 N. Maurice River Pkwy., Vineland, N.J. 08360

[ * ] Notice: The portion of the term of this patent subsequent to May 13, 1997, has been disclaimed.

[21] Appl. No.: 876,062

[22] Filed: Feb. 8, 1978

Related U.S. Application Data

[63] Continuation-in-part of Ser. No. 525,844, Nov. 21, 1974, abandoned, which is a continuation-in-part of Ser. No. 139,844, May 3, 1971, abandoned.

[51] Int. Cl.$^3$ ................... A01N 43/64; A01N 33/12
[52] U.S. Cl. ........................................ 71/67; 424/76; 424/244; 424/249; 424/273 R; 424/329
[58] Field of Search ............... 424/329, 244, 249, 273, 424/76; 71/67

[56] References Cited

U.S. PATENT DOCUMENTS 3,198,251 8/1965 Shore .................................... 424/76
3,282,776 11/1966 Kitzke et al. ..................... 424/76 X

OTHER PUBLICATIONS

Schwartz & Perry–"Surface Active Agents", vol. 1, pp. 162, 452 & 453, (1949).
Chemical Abstracts 53: 4771i, (1959).
Chemical Abstracts 52: 17632d, (1958).
Chemical Abstracts, 7th Coll. Index 22,387s, 1962–1966.

*Primary Examiner*—Leonard Schenkman
*Attorney, Agent, or Firm*—Hammond & Littell, Weissenberger and Muserlian

[57] ABSTRACT

Novel bactericidal water-soluble complexes comprising a quaternary ammonium salt and a tricyclic, cage-type heterocycle containing four nitrogen atoms in molar ratios of 1:4 and 3:2 which are effective against both gram negative and gram positive bacteria, fungi, molds, and algae and to a novel method of killing same and novel pesticidal compositions.

25 Claims, No Drawings

BACTERICIDAL WATER-SOLUBLE COMPLEXES

PRIOR APPLICATIONS

This application is a continuation-in-part of my copending, application Ser. No. 525,844 filed Nov. 21, 1974, now abandoned, which was a continuation-in-part of my application Ser. No. 139,844 filed May 3, 1971, now abandoned.

STATE OF THE ART

The present trend in pest control is to use synergists to increase the effectiveness of a pesticide rather than to increase the dosage or to develop new and more toxic compounds. Synergistic mixtures have been commercially used for herbicides and insecticides, but synergistic mixtures have not been commercially developed for bactericidal and fungicidal purposes.

Organic mercury and tin salts have been used to control bacteria and fungi but are not generally used due to their high degree of toxicity and prolonged persistence. Phenols are not as effective as the other germicides commercially available, and so larger quantities are needed at which level their strong odor becomes annoyingly obvious. Quaternary ammonium salts have been used to combat bacteria, fungi, molds, and algae but are readily inactivated by organic debris, for they form insoluble complexes and are thereby removed from the arena of combat so that overdoses are needed for the required efficacy. Oxidizing agents such as peroxides and hypochlorites are also inactivated by organic debris.

OBJECTS OF THE INVENTION

It is an object of the invention to provide novel bactericidal complexes and bactericidal compositions containing the said complexes.

It is another object of the invention to provide a novel method of killing microorganisms.

It is a further object of the invention to control odors caused by bacterial decomposition of organic matter.

These and other objects and advantages of the invention will become obvious from the following detailed description.

THE INVENTION

The novel biocidal complexes are comprised of one of the complexes of a quaternary ammonium salts and a tricyclic, cage-type heterocycle containing four nitrogen atoms in the molar ratios 1:4 and 3:2. Biocidal compositions containing the said complexes may be in any suitable form such as solutions or suspensions, sprays, aerosols, concentrates, emulsions, powders, etc.

Various quaternary ammonium salts are known to be mild disinfectants and are generally prepared by reacting an alkyl halide, sulfonate or sulfate with a tertiary base. The usual salts are the halides such as the chloride or bromide, sulfates, methanesulfonates, ethanesulfonates, and benzenesulfonates.

Among the preferred quaternary ammonium salts for the compositions of the invention are those having the formula

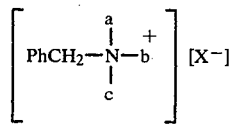

wherein Ph is an aromatic nucleus with the necessary pi electron resonance, X is selected from the group of organic and inorganic anions including halogens, selected from the group consisting of halides, sulfate, lower alkyl sulfates, alkanesulfonates and benzenesulfonates with or without nucleus substitutions. These and other suitable quaternary ammonium salts are described in Schwartz et al., Surface Active Agents and Detergents, Vol. II, (1958), pp. 112 to 118.

The tricyclic, cage-type heterocycles having four nitrogen atoms are prepared by the condensation of formaldehyde with ammonia or a primary diamine in which the two amino groups are separated by an alkylene chain of 1 to 2 carbon atoms. Examples of suitable diamines are ethylenediamine, 1,2-diaminopropane, o-phenylenediamines, with or without ring substitutions, etc. The condensation of formaldehyde and ammonia forms in situ a temporary methylenediamine. Specific heterocycles are hexamethylenetetraamine, 1,3,6,8-tetraazatricyclo-(4,4,1,1$^{3.8}$)-dodecane, 4,5,9,10-dibenzo-1,3,6,8-tetraazatricyclo-(4,4,1,1$^{3.8}$)-dodecane 4(5),9(10)-dimethyl-1,3,6,8-tetraazatricyclo-(4,4,1,1$^{3.8}$)-dodecane and 4(5), 9(10),-dimethyl-4,5,9,10-dibenzo-1,3,6,8-tetraazatricyclo-(4,4,1,1$^{3.8}$)-dodecane.

The two individual components of the complex have a weak bactericidal activity but the combination of the two components into a complex results in a bactericidal complex having an activity much greater than the sum of the equivalent activity of the individual components. The complexes contain the quaternary ammonium salts and heterocycle in a molar ratio of 1:4 and 3:2, which cover complexes of 5 molecules; with other proportions, the activity of the compositions drops off dramatically. The compositions may contain mixtures of the two complexes.

The highly effective activity of these complexes is believed to be due to their stability and solubility. They are stable under standard conditions and do not react with inert matter such as blood, feces, and other organic debris, but inside of the biologically active system of the microorganism, they break down and become sufficiently reactive to interfere with the cell's metabolic pathways.

The complexes formed are compositions ranging from four moles of heterocycle and one mole of a benzalkonium salt up to three moles of the benzalkonium salt to two moles of the heterocycle. Thus, these complexes range from simple two molecule complexes up to a total of five molecules. The number of molecules seems to be limited by the size of these molecules, for too large molecules block access of the balance to the second component, and the complex bonding cannot form. The tendency seems to favor the formation of the largest complex possible with a limit of five molecules. Where two stable complexes could form from the mixture of components available, there will be a greater time lag for their formation while the two complexes are competing for the available components.

The biocidal compositions of the invention may contain any conventional carrier such as water, aqueous alcohols, organic solvents; compatible enzymes; wetting agents; emulsifiers; perfumes; and other standard ingredients for bactericidal compositions.

The novel method of the invention for killing microorganisms comprises contacting these organisms with a lethal amount of a complex comprised of a benzalkonium salt and a tricyclic, cage-type heterocycle containing four nitrogen atoms. The complexes may be used in hospitals, in agriculture, in treating stored wastes, in the reduction of microbial slime in paper mill water systems, etc.

The novel method of the invention for preventing odors due to bacterial decomposition of organic matter comprises admixing the organic matter with a biocidal amount of any of the complexes of a quaternary ammonium salts with a tricyclic, cage-type heterocycle containing four nitrogen atoms. The organic matter may be any organic matter which produces undesirable odors upon decomposition. Examples are urine from cats and other domestic animals, manure from fowl, cattle, horses, etc., garbage, etc., or inert matter to be later contaminated with the organic matter and/or microorganisms such as cat litter.

In the following examples there are described several preferred embodiments to illustrate the invention. However, it should be understood that the invention is not intended to be limited to the specific embodiments.

EXAMPLE 1

A solution was prepared with 15 g of hexamethylenetetraamine and 12.5 g of 80% alkyldimethylbenzylammonium chloride (alkyl of 12 to 18 carbon atoms for a theoretical molecular weight of 366) in 1 l of water. After 24 hours, the water was carefully evaporated to leave 25 g of residue. The residue was a white, crystalline substance that decomposed at 240° C. Titration of a solution of this product with silver nitrate solution according to the method described on Page 59 in Official Methods of Analysis of the Association of Official Agricultural Chemists, 10th Edition (1965) found this product to be a complex of four moles of hexamethylenetetraamine with one mole of the benzalkonium chloride.

EXAMPLE 2

The procedure of Example 1 was followed using 1 g of hexamethylenetetraamine and 6.0 g of the benzalkonium chloride of Example 1 (equivalent to 4.8 g of pure compound) in 250 ml water to obtain 5.8 g of the complex comprised of 2 moles of hexamethylenetetraamine and 3 moles of benzalkonium chloride.

EXAMPLE 3

Using the procedure of Example 1, similar complexes were prepared with alkyldimethylbenzylammonium salts, alkyldimethyl-(ethylbenzyl)-ammonium salts, dodecyldimethyl-(1-naphthylmethyl)-ammonium chloride, (diisobutylphenoxy)-ethoxyethyldimethylbenzylammonium chloride, (methyldodecyl)-benzyltrimethylammonium chloride; etc. as the benzalkonium component. The heterocyclic component came from the group of tricyclic, cage-type heterocycles having four nitrogen atoms prepared by the condensation of formaldehyde with ammonia or a primary diamine with the two amino groups separated by an alkylene chain of 1 to 2 carbon atoms. Examples of these are hexamethylenetetraamine, a commercial product, 1,3,6,8-tetraazatricyclo-(4,4,1,1$^{3.8}$)-dodecane, described by Bischoff, Berichte 31 3248 (1898) whose proposed structure was almost the correct one presented by Volpp in Berichte 95 1493–1494 (1962), 4,5,9,10-dibenzo-1,3,6,8-tetraazatricyclo-(4,4,1,1$^{3.8}$)-dodecane, and 4(5),9(10-dimethyl-4,5,9,10-dibenzo-1,3,6,8-tetraazatricyclo-(4,4,1,1$^{3.8}$)-dodecane, both of which were described by Fischer in Berichte 25 2711–2713 with the structures clarified by Volpp, op. cit.

EXAMPLE 4

The formation of the complexes could also be shown by a bioassay method. Thus, a 24 hour culture of *Staphylococcus aureus* in nutrient solution was placed into sterile flasks and sufficient amounts of benzyldimethyltetradecylammonium chloride (Column A) and hexamethylenetetraamine or HMTA (Column B) were added thereto to obtain a concentration of 5 ppm. The control contained no active ingredient and all the flasks were incubated at 35° C. for 4 hours, after which they were plated out on nutrient agar in petri plates and incubated for 48 hours at 35° C. The results are reported in Table I as a percentage of control of the microorganisms.

TABLE I

| | Active Product | |
|---|---|---|
| A % by weight | B % by weight | % Control |
| 0 | 0 | 0 |
| 0 | 100 | 29.14 |
| 5 | 95 | 39.74 |
| 10 | 90 | 45.70 |
| 15 | 85 | 50.99 |
| 20 | 8 | 57.62 |
| 40 | 60 | 92.11 |
| 50 | 50 | 29.59 |
| 60 | 40 | 52.63 |
| 80 | 20 | 99.96 |
| 85 | 15 | 50.33 |
| 90 | 10 | 37.09 |
| 95 | 5 | 35.43 |
| 100 | 0 | 30.46 |

From these data, it can be seen that the individual components do possess some bactericidal activity at 5 ppm even after 4 hours of contact. The 1:1 by weight mixture of these two components totalling 5 ppm should have the same activity, and this is shown to be true in Table I, and so any improvement of this activity by any of the other mixtures would represent new and unexpected activity. Such new and unexpected activity seems to peak at the weight ratios 4:1 and 2.3:, with an activity of about 250% greater than that of either component or the 1:1 by weight mixture of both.

The 2:3 weight ratio of components is equivalent to a complex comprised of 1 mole of benzalkonium chloride with 4 moles of HMTA. The peak activity indicates the correct proportions of both components to form 5 ppm of complex. The loss of activity as the proportions change indicates a reduction in the amount of complex formed through a lack of sufficient quantity of the second component.

The 4:1 weight ratio of components is equivalent to a complex consisting of 3 moles of benzalkonium chloride and 2 moles of HMTA. Both of these complexes consist of 5 molecules each. These two complexes seem to be the ones favored by this particular choice of components, and this evidence was confirmed experimentally. Other molar ratios are less effective since they are reduce the concentration of the effective complex by providing an excess of the second component.

EXAMPLE 5

In order to demonstrate that these complexes are effective against both gram negative and gram positive bacteria, the bactericidal activity was determined using the standard evaluation test for quaternary ammonium salts described in Official Methods of Analysis of the Association of Official Agricultural Chemists, 10th Edition (1965), pages 80–82, with a 15 minute exposure of *Staphylococcus aureus* (SA) and *Salmonella typhosa* (ST) to the complex of 4 moles of the heterocycle 1,3,6,8-tetraazatricyclo-(4,4,1,1$^{3.8}$)-dodecane (B) and 1 mole of alkylbenzyldimethylammonium chloride (alkyl with 12 to 18 carbon atoms) (A) and reported in Column C.

TABLE II

| Concentrations | SA | | | ST | | |
| --- | --- | --- | --- | --- | --- | --- |
| | A | B | C | A | B | C |
| 1:1,000 | + | + | − | − | + | − |
| 1:5,000 | + | + | − | − | + | − |
| 1:10,000 | + | + | − | + | + | − |
| 1:15,000 | + | + | + | + | + | + |
| 1:20,000 | + | + | + | + | + | + |

The results are reported in Table II with + indicating bacterial growth (insufficient to prevent even some growth) and − indicating 100% control under the conditions of this test.

The results of Table II show that the complex tested is effective against both gram negative and gram positive bacteria. The effective control of *Staphylococcus aureus* indicates that this complex can be used in hospital cleaning solutions as a disinfectant. This is a significant development since both of the individual components were ineffective alone.

Similar results were obtained from the same test using the complex containing 4,5,9,10-dibenzo-1,3,6,8-tetraazatricyclo-(4,4,1,1$^{3.8}$)-dodecane as the heterocycle.

EXAMPLE 6

To demonstrate superior efficacy of the complex in the presence of organic debris, a germicide test was carried out on *Staphylococcus aureus* with the addition of sterile organic matter prepared from chicken feces and incorporated at the rate of 10% of the nutrient medium. Two commercial quaternary ammonium germicides were employed as standards. The results are reported as percentage of control in Table III.

TABLE III

Germicidal activities of some quaternary ammonium chlorides including one in the form of a complex in the presence of organic matter (10% chicken feces). Data evaluated as percent control. Concentration of toxicant is 100 ppm.

| Contact Time Hours | 2 | 4 | 24 | 28 | 48 |
| --- | --- | --- | --- | --- | --- |
| alkyldimethylbenzylammonium chloride 5% alkydimethylethylbenzylammonium chloride 5% | 0 | 42.5 | 30.7 | 49.5 | 0 |
| alkyldimethylbenzylammonium chloride 10% in bimolecular complex with HMTA (1:4 molar ratio) | 50 | 46.9 | 95.6 | 96 | 98.5 |
| Contact Time in Hours | 2 | 5 | 8 | 25 | 32 |
| alkyldimethylbenzylammonium chloride 10% | 95.9 | 91.8 | 92.1 | 36.1 | 33.3 |
| alkyldimethylbenzylammonium chloride 10% in bimolecular complex with HMTA (1:4 molar ratio) | 66.6 | 66.6 | 82.2 | 100 | 100 |

It is obvious that the complex is not inactivated by the presence of organic debris while both of the uncomplexed quaternary ammonium salts were inactivated.

EXAMPLE 7

An aqueous solution containing 25% by weight of the complex described in Example 1 was sprayed about a basement with mildew from high humidity conditions. After spraying the typical musty odor disappeared and remained away for 6 months. This indicates an effective residue of the complex not inactivated by the presence of cellulose (wood).

EXAMPLE 8

A solution of 25 parts by weight of 1,3,5,7-tetraazatricyclo-(3,3,1,1$^{3.7}$)-decane in 52 parts by weight of water was added to a solution of 0.5 parts by weight of perfume, 10.0 parts by weight of a polyethylene oxide-alkylphenol adduct as an emulsifier and 12.5 parts by weight of technical (80%) alkyldimethylbenzylammonium chloride (alkyl of 12 to 18 carbon atoms) to form a clear solution.

The solution of this Example was prepared again with the exception of the heterocycle so that the 1,3,6,8-tetraazatricyclo-(4,4,1,1$^{3.8}$)-dodecane was substituted. The solution of this Example was prepared again with 4,5,9,10-dibenzo-1,3,6,8-tetraazatricyclo-(4,4,1,1$^{3.8}$)-dodecane as the heterocycle. In each case, the appropriate complex formed in situ.

EXAMPLE 9

A solution of 25 parts by weight 1,3,5,7-tetraazatricyclo-(3,3,1,1$^{3.7}$)-decane in 75 parts by weight of water was added to a solution of 125 parts by weight of technical (80%) alkyldimethylbenzylammonium chloride (alkyl 8 to 18 carbon atoms), 100 parts by weight of polyethylene oxide-alkylphenol adduct, 25 parts by weight of perfume, 30 parts by weight of p-dichlorobenzene, and 120 parts by weight of o-dichlorobenzene to form a clear solution. This solution was then diluted 10 times with alcohol and placed in aerosol cans with the correct amount of propellant of an inert type such as the Freon (halocarbon) type, carbon dioxide, or butane.

EXAMPLE 10

A solution of 5 parts by weight of 1,3,5,7-tetraazatricyclo-(3,3,1,1$^{3.7}$)-decane, 20 parts by weight of alkyldimethylbenzylammonium chloride, 43 parts by weight of water, 2 parts by weight of sodium carbonate, 15 parts by weight of polyethylene oxidealkylphenol adduct, 14 parts by weight of technical N,N-diethanolamides of long-chain fatty acids, and 1 part by weight of perfume was prepared and then diluted with water 400 times before use.

EXAMPLE 11

A solution containing 25 parts by weight of hexamethylenetetraamine, 20 parts by weight of alkyldimethylbenzylammonium acetate (alkyl 8 to 18 carbon atoms), 5 parts by weight of polyethylene oxide-alkylphenol adduct, 8 parts by weight of perfume, 0.2 parts by weight of a water-soluble blue dye, and 41.8 parts by weight of water was prepared.

EXAMPLE 12

A solution containing 96.8 parts by weight of hexamethylenetetraamine, 60.5 parts by weight of 80% alkyldimethylbenzylammonium chloride (alkyl has 8 to 18 carbon atoms), 36.3 parts by weight of technical 2-alkyloxazoline (alkyl has 8 to 18 carbon atoms), 24.2 parts by weight of perfume, 24.2 parts by weight of 30% silicone defoamer, and 242.1 parts by weight of water was prepared as a non-foaming product.

EXAMPLE 13

A solution of 96.8 parts by weight of hexamethylenetetraamine, 58.08 parts by weight of 80% alkyltrimethylbenzylammonium chloride (alkyl has 8 to 18 carbon atoms), 96.8 parts by weight of polyethylene oxide-alkylphenol) adduct, 24.2 parts by weight of perfume, 19.36 parts by weight of 2-ethyl-1,3-hexanediol, 16.2 parts by weight of o-dichlorobenzene, 8 parts by weight of p-dichlorobenzene, and 164.56 parts by weight of water was prepared. This formulation was found to be effective for the control of septic conditions in sewage lagoons and the putrefaction of garbage and other organic wastes at canning factories, supermarkets, hamburger stands, and restaurants. It was interesting to observe people consuming food and drink parked next to garbage bins, which, if untreated, would have been producing unappetizing odors.

EXAMPLE 14

A 25% solution of the complex of Example 1 in water was added to a swimming pool pea green with algae. The product was added at the rate of 5 ppm 10 P.M. and by 8 A.M. the next morning, the pool was completely clear and ready for use.

EXAMPLE 15

The bactericidal activity was determined using the standard evaluation test for quaternary ammonium compounds described in Official Methods of Analysis of the Association of Official Agricultural Chemists, 10th edition (1965), p. 80–82 with a 15 minute exposure to Pseudomonas aeruginosa PRD-10. The compounds tested with increasing dilution were alkyl dimethyl benzyl ammonium chloride where alkyl was a mixture of $C_{12}$ to $C_{14}$ (A); hexamethylene tetramine (B) and a 1:1 weight ratio of the said chloride and hexamethylene tetramine (C). The results are reported in Table IV with + being no control (insufficient to prevent even some growth) and − being 100% control under the conditions of the test.

TABLE IV

| Concentration | A | B | C |
|---|---|---|---|
| 1: 3,200 | − | + | − |
| 1: 6,400 | − | + | − |
| 1:12,800 | + | + | − |
| 1:25,600 | + | + | − |
| 1:51,200 | + | + | + |

Table IV shows that in this test hexamethylenetetraamine had no bactericidal activity but increased the bactericidal activity of alkyldimethylenezylammonium chloride four times. This is a clear demonstration of increased activity.

EXAMPLE 16

A mixture of 25 parts by weight of hexamethylenetetraamine and 52 parts by weight of water was added with stirring to a mixture of 0.5 parts by weight of perfume, 10.0 parts by weight of a polyethylene oxide-alkylphenol adduct as an emulsifier and 12.5 parts by weight of alkyl dimethylbenzyl ammonium chloride (alkyl of 12 to 16 carbon atoms) to form a clear solution. 1 to 2 ml of solution was admixed with 1 pound of kitty litter which was used by two adult cats in a closed room for one week. During this time, there was none of the odor typical of microbial decomposition of urine.

EXAMPLE 17

The solution prepared in Example 3 was sprayed about the interior of chicken coops and particularly on the manure covered floors. The strong objectionable odor of chicken manure was eliminated almost immediately after the spraying.

EXAMPLE 18

A solution containing 6 parts by weight of 1,3,5,7-tetraazatricyclo-(3,3,1,1$^{3.7}$)-decane, 2.5 parts by weight of 80% alkyldimethylbenzylammonium chloride, 0.5 parts by weight of sodium acetate, 2 parts by weight of sodium carbonate, 0.5 parts by weight of perfume, 2.5 parts by weight of N,N-diethanolamide of long chain fatty acids (up to 18 carbon atoms), 5 parts by weight polyethylene oxide-alkylphenol adduct, 20 parts by weight of sodium lauryl sulfate concentrate (35% active), and 61 parts by weight of water was prepared.

EXAMPLE 19

A mixture containing 25 parts by weight of 1,3,5,7-tetraazatricyclo-(3,3,1,1$^{3.7}$)-decane, 15 parts by weight of alkyldimethyl(1-naphthylmethyl)-ammonium chloride (alkyl has 12 to 14 carbon atoms) monohydrate, 10 parts by weight of sodium lauryl sulfate was prepared by a dry formulation.

EXAMPLE 20

A solution of 96.8 parts by weight of 1,3,5,7-tetraazatricyclo-(3,3,1,1$^{3.7}$)-decane, 58.08 parts by weight of 80% alkyltrimethylbenzylammonium chloride (alkyl has 8 to 18 carbon atoms), 96.8 parts by weight of polyethylene-oxide-alkylphenol adduct, 24.2 parts by weight of perfume, 19.36 parts by weight of 2-ethyl-1,3-hexanediol, 16.2 parts by weight of o-dichlorobenzene, 8 parts by weight of p-dichlorobenzene and 164.56 parts by weight of water was prepared.

EXAMPLE 21

The following solutions were prepared and tested as garbage odor inhibitors as in Example 7 and were found to be effective to control odor produced by bacteria decomposing the organic matter.

Solution 1

10% by weight of hexamethylenetetraamine
12% Culversan LC 80 (CULVER CORP.)
18% Emulsifier of Example 3
22% Water
4.5% Perfume
2.5% 2-ethyl-1,3-hexanediol as insect repellant
2.5% lindane 4.0% p-dichlorobenzene
24.5% methylated naphthalene Solution 2

4% by weight of p-dichlorobenzene
18% Neutronyx 600
2.5% lindane
2.5% insect repellant (N,N-diethyl-m-toluamide)
10% Culversan LC 80
12% hexamethylenetetraamine
5% Perfume
22% water
24% Mineral Oil Solution 3

20% by weight of hexamethylenetetraamine
15% Culversan LC 80
10% Emulsifier of Example 3
5% Perfume
5% N,N-diethyl-m-toluamide
45% Water Solution 4

24% by weight of petroleum base
22% Water
20% Emulsifier of Example 3
10% Culversan LC 80
10% hexamethylenetetraamine
5% p-dichlorobenzene
5% Perfume
2% 2-ethyl-1,3-hexanediol Solution 5

20% by weight of hexamethylenetetraamine
12½% by weight of alkyldimethylbenzylammonium acetate (alkyl of 12 to 18 carbon atoms) made by equimolar amounts of Culversan LC 80 and sodium acetate
67½% by weight of Water Various modifications of the products and compositions of this invention may be made without departing from the spirit or scope thereof, and it is understood that the invention is to be limited only as defined in the appended claims.

I claim:

1. A water-soluble complex comprising a quaternary ammonium salt and a tricyclic, cage-type heterocycle containing four nitrogen atoms selected from the group consisting of hexamethylenetraamine, 1,3,6,8-tetraazatricyclo-(4,4,1,1³·⁸)-dodecane, 4,5,9,10-dibenzo-1,3,6,8-tetraazatricyclo-(4,4,1,1³·⁸)-dodecane and 4(5), 9(10)-dimethyl-1,3,6,8-tetraazatriccylo-(4,4,1,1³·⁸)-dodecane in molar ratios of 1:4 and 3:2.

2. A complex of claim 1 wherein the quaternary ammonium salt has the formula

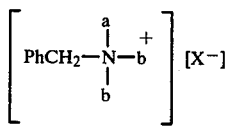

wherein Ph is phenyl, X is selected from the group of organic and inorganic anions selected from the group consisting of halides, sulfate, lower alkyl sulfates, alkanesulfonates and benzenesulfates.

3. The complex of claim 1 wherein the heterocycle is hexamethylenetetraamine.

4. The complex of claim 1 wherein the heterocycle is 1,3,6,8-tetraazatricyclo-(4,4,1,1³·⁸)-dodecane.

5. The complex of claim 1 wherein the heterocycle is 4,5,9,10-dibenzo-1,3,6,8-tetraazatricyclo-(4,4,1,1³·⁸)-dodecane.

6. The complex of claim 1 wherein the said molar ratio is 1:4.

7. The complex of claim 1 wherein the said molar ratio is 3:2.

8. A water soluble complex of claim 1 wherein the heterocycle is hexamethylenetetraamine and the quaternary ammonium salt is an alkyl dimethylbenzyl ammonium chloride with the alkyl having 12 to 18 carbon atoms.

9. A complex of claim 3 wherein the quaternary ammonium salt is selected from the group consisting of dodecyldimethyl-(1-naphthylmethyl)-ammonium chloride, (diisobutylphenoxy)-ethoxyethyldimethylbenzylammonium chloride, (methyldodecyl)-benzyltrimethylammonium chloride.

10. A biocidal composition comprising a biocidally effective amount of at least one complex of claim 1 and an inert carrier.

11. A composition of claim 10 wherein the quaternary ammonium salt has the formula

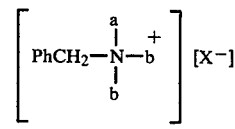

wherein Ph is phenyl, X is selected from the group organic and inorganic anions selected from the group consisting of halides, sulfate, lower alkyl sulfates, alkanesulfonates and benzenesulfates.

12. A composition of claim 10 wherein the heterocycle is hexamethylenetetraamine.

13. A composition of claim 10 wherein the heterocycle is 1,3,6,8-tetraazatricyclo-(4,4,1,1³·⁸)-dodecane.

14. The composition of claim 10 wherein the heterocycle is 4,5,9,10-dibenzo-1,3,6,8-tetraazatricyclo-(4,4,1,1³·⁸)-dodecane.

15. The composition of claim 10 wherein the said molar ratio is 1:4.

16. The composition of claim 10 wherein the said molar ratio is 3:2.

17. A method of killing microorganisms comprising contacting the microorganisms with a lethal amount of a complex of claim 1.

18. A method of claim 17 wherein the quaternary ammonium salt has the formula

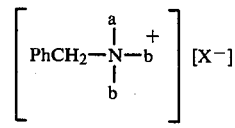

wherein Ph is phenyl, X is selected from the group organic and inorganic anions selected from the group consisting of halides, sulfate, lower alkyl sulfates, alkanesulfonates and benzenesulfates.

19. A method of claim 17 wherein the heterocycle is selected from the group consisting of hexamethylenetetraamine, 1,3,6,8-tetraazatricyclo-(4,4,1,1$^{3.8}$)-dodecane, 4,5,9,10-dibenzo-1,3,6,8-tetraazatricyclo-(4,4,1,1$^{3.8}$)-dodecane and 4(5), 9(10)-dimethyl-1,3,6,8-tetraazatricyclo-(4,4,1,1$^{3.8}$)-dodecane.

20. The method of claim 17 wherein the heterocycle is hexamethylenetetraamine.

21. The method of claim 17 wherein the heterocycle is 1,3,6,8-tetraazatricyclo-(4,4,1,1$^{3.8}$)-dodecane.

22. The method of claim 17 wherein the heterocycle is 4,5,9,10-dibenzo-1,3,6,8-tetraazatricyclo-(4,4,1,1$^{3.8}$)-dodecane.

23. The method of claim 17 wherein the said molar ratio is 1:4.

24. The method of claim 17 wherein the said molar ratio is 3:2.

25. A method of preventing odors due to bacterial decomposition of organic matter comprising contacting organic matter with a bactericidally effective amount of a complex of claim 1.

* * * * *